US008089622B2

(12) United States Patent
Birkner et al.

(10) Patent No.: US 8,089,622 B2
(45) Date of Patent: Jan. 3, 2012

(54) DEVICE AND METHOD FOR EVALUATING DEFECTS IN THE EDGE AREA OF A WAFER AND USE OF THE DEVICE IN INSPECTION SYSTEM FOR WAFERS

(75) Inventors: Andreas Birkner, Jena (DE); Michael Hofmann, Heuchelheim (DE); Wolfgang Vollrath, Burbach (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 980 days.

(21) Appl. No.: 12/039,047

(22) Filed: Feb. 28, 2008

(65) Prior Publication Data

US 2008/0232672 A1  Sep. 25, 2008

Related U.S. Application Data

(60) Provisional application No. 60/895,763, filed on Mar. 20, 2007.

(30) Foreign Application Priority Data

Mar. 19, 2007 (DE) .......................... 10 2007 013 646
May 24, 2007 (DE) .......................... 10 2007 024 525

(51) Int. Cl.
*G01N 21/00* (2006.01)
*G06K 9/62* (2006.01)
(52) U.S. Cl. ..................................... 356/237.5; 382/147
(58) Field of Classification Search .... 356/237.1–237.5; 382/144–149
See application file for complete search history.

(56) References Cited

U.S. PATENT DOCUMENTS

| 6,947,588 | B2 * | 9/2005 | Sim ................................ 382/149 |
| 7,149,341 | B2 * | 12/2006 | Hayashi et al. ............... 382/145 |
| 7,280,197 | B1 * | 10/2007 | Rosengaus ................. 356/237.1 |
| 7,340,087 | B2 * | 3/2008 | Watkins et al. ............... 382/145 |
| 7,366,344 | B2 * | 4/2008 | Sim ................................ 382/149 |
| 7,403,278 | B2 * | 7/2008 | Hayashi et al. ............ 356/237.1 |
| 7,616,804 | B2 * | 11/2009 | Pai et al. ....................... 382/145 |
| 7,706,599 | B2 * | 4/2010 | Sim ................................ 382/149 |
| 7,800,748 | B2 * | 9/2010 | Sakaguchi ................. 356/237.2 |
| 7,822,260 | B2 * | 10/2010 | Watkins et al. ............... 382/145 |
| 2003/0169916 | A1 | 9/2003 | Hayashi et al. |
| 2005/0013474 | A1 * | 1/2005 | Sim ................................ 382/145 |
| 2005/0023491 | A1 | 2/2005 | Young et al. |
| 2005/0036671 | A1 * | 2/2005 | Watkins et al. ............... 382/145 |
| 2006/0115142 | A1 * | 6/2006 | Sim ................................ 382/145 |

(Continued)

FOREIGN PATENT DOCUMENTS

DE  10313202 B3  10/2004

*Primary Examiner* — Patrick J Connolly
(74) *Attorney, Agent, or Firm* — Houston Eliseeva, LLP

(57) ABSTRACT

A device for evaluating defects in the edge area of a wafer (6) is disclosed. The evaluation may also be performed automatically. In particular, the device includes three cameras (25, 26, 27), each provided with an objective (30), wherein a first camera (25) is arranged such that the first camera (25) is opposite to an edge area on the upper surface (6*a*) of the wafer (6), wherein a second camera (26) is arranged such that the second camera (26) is opposite to a front surface (6*b*) of the wafer (6), and wherein a third camera (27) is arranged such that the third camera (27) is opposite to an edge area on the lower surface (6*c*) of the wafer (6).

20 Claims, 10 Drawing Sheets

U.S. PATENT DOCUMENTS

| | | |
|---|---|---|
| 2006/0119366 A1 | 6/2006 | Iffland et al. |
| 2007/0258085 A1* | 11/2007 | Robbins et al. ............ 356/237.4 |
| 2008/0013822 A1* | 1/2008 | Pai et al. ....................... 382/145 |
| 2008/0079932 A1* | 4/2008 | Yokota ........................ 356/237.1 |
| 2008/0204756 A1* | 8/2008 | Sim ............................... 356/445 |
| 2008/0212084 A1* | 9/2008 | Watkins et al. ............ 356/237.5 |
| 2008/0232672 A1* | 9/2008 | Birkner et al. ................ 382/145 |
| 2009/0086483 A1* | 4/2009 | Hahn et al. ..................... 362/235 |
| 2009/0116727 A1* | 5/2009 | Jin et al. ........................ 382/149 |
| 2009/0122304 A1* | 5/2009 | Jin et al. ..................... 356/237.4 |
| 2009/0279080 A1* | 11/2009 | Danner et al. ............. 356/237.3 |

* cited by examiner

DEVICE AND METHOD FOR EVALUATING DEFECTS IN THE EDGE AREA OF A WAFER AND USE OF THE DEVICE IN INSPECTION SYSTEM FOR WAFERS

RELATED APPLICATIONS

This application claims priority to German Patent Application No. 10 2007 013 646.5, filed on Mar. 19, 2007, and German Patent Application No. 10 2007 024 525.6, filed on May 24, 2007, and claims the benefit under 35 USC 119(e) of U.S. Provisional Application No. 60/895,763 filed on Mar. 20, 2007, all of which are incorporated herein by reference in their entirety.

FIELD OF THE INVENTION

The present invention relates to a device for visually evaluating defects in the edge area of a wafer. In particular, the device for visually evaluating defects in the edge area of a wafer includes a first camera arranged such that the first camera is opposite to an edge area on the upper surface of the wafer. A second camera is arranged such that the second camera is opposite to a front surface of the wafer. A third camera is arranged such that the third camera is opposite to an edge area on the lower surface of the wafer. Each camera has a field of view for acquiring images of the defects.

The present invention further relates to a method for visually evaluating defects in the edge area of a wafer. For the method for visually evaluating defects in the edge area of a wafer, a review of the defects in the area is performed with a first camera opposite to an upper edge area of the wafer, a second camera opposite to the front surface of the wafer, and a third camera opposite to a lower edge area of the wafer.

The invention further relates to the use of the device in an inspection system for wafers. The inspection system for wafers includes at least one unit for micro-inspection, transport means and alignment means. There is further provided at least one display, on which acquired and/or stored images of the defects may be displayed to a user.

BACKGROUND OF THE INVENTION

U.S. patent application 2005/0013474 discloses a device also inspecting or examining the edge area of a wafer with three cameras. For the inspection of the wafer edge, the wafer is rotated past the cameras more than two times. There is also provided a bright field arrangement for the illumination of the wafer. However, the cameras are not arranged on a common carrier, and the cameras are further not intended to be brought closer to the wafer edge in order to achieve a better positioning of the edge of the wafer with respect to the cameras. In addition, there is no indication that single defects may be directly approached by the device disclosed therein, so that an image of these defects may be acquired by the cameras.

U.S. patent application 2003/0169916 discloses a device using three cameras for acquiring an image of the front surface of the wafer edge and of the two bevels at the wafer edge, respectively. The cameras are arranged such that a first camera is opposite to the upper bevel of the wafer edge, that a second camera is opposite to the front surface of the wafer, and that a third camera is opposite to the lower bevel of the wafer edge. The cameras are oriented such that they face the respective associated surfaces at a right angle. However, the application does not disclose that the cameras are arranged on a common carrier movable in a perpendicular direction with respect to the edge of the wafer in order to position the cameras suitably for image acquisition. In addition, the first camera and the third camera are not arranged to image the upper surface and the lower surface, respectively, of the wafer edge nor to record defects there and display them to the user.

SUMMARY OF THE INVENTION

It is thus the object of the present invention to provide a device allowing the inspection of the defects on the upper surface, the front surface and the lower surface of the wafer edge in a simple way.

This object is achieved by a device including at least one illumination means designed such that the first, second and third cameras are arranged in bright field arrangement. The wafer is positionable in the field of view of each camera for acquiring the image of the defect.

It is a further object of the invention to suggest a method by which images of defects may be acquired, wherein the defects are located in the edge area of the wafer. The inventive method is supposed to allow displaying the selected defects to a user for inspection.

The method for evaluating defects in the edge area of a wafer with a first camera opposite to an upper edge area of the wafer, a second camera opposite to the front surface of the wafer, and a third camera opposite to a lower edge area of the wafer is characterized by the steps of:

depositing a wafer on a prealigner by means of a robot, moving at least a first camera and a third camera in a radial direction with respect to the edge of the wafer so that the edge area of the wafer gets into the field of view of the respective camera, positioning the wafer based on stored and/or determined position data such that the defects on the edge of the wafer are aligned with the field of view of the first and/or the second and/or the third camera for visual evaluation, and beginning image acquisition with at least one of the cameras depending on the position of the defect opposite to the upper edge area of the wafer or the lower edge area of the wafer or the front surface of the wafer, wherein each defect to be captured is illuminated in the bright field.

It is a further object of the present invention to suggest the use of a device for visually evaluating defects in the edge area of a wafer in inspection system for wafers.

The use has the advantage that the alignment means is associated with the device for visually evaluating defects in the edge area of the wafer provided with three cameras. A first camera is arranged such that the first camera is opposite to an edge area on the upper surface of the wafer. A second camera is arranged such that the second camera is opposite to a front surface of the wafer. A third camera is arranged such that the third camera is opposite to an edge area on the lower surface of the wafer.

The device for visually evaluating defects in the edge area of the wafer is particularly advantageous because at least two of the three cameras are designed movable in the direction towards the wafer edge. Thus optimal positioning of the cameras with respect to the upper surface of the wafer edge and the lower surface of the wafer edge may be achieved. It is also contemplated that the camera opposite to the front edge area of the wafer, together with the two other cameras, is arranged on a common carrier, which is designed movable in a perpendicular direction with respect to the wafer edge. There is also provided an illumination device arranged such that a bright field arrangement is achieved together with the cameras. The first, second and/or third camera acquires an image of a defect in the edge area of the wafer with a defined field of view size. The position coordinates of the defect in the edge area of the wafer are known, so that the wafer is moved into position with respect to the cameras according to these coordinates, so that, depending on the position of the defect, the image of the defect is acquired either on the upper surface of the wafer edge or on the lower surface of the wafer edge or on the front surface of the wafer edge.

In an advantageous embodiment of the invention, the first camera and the third camera are arranged on a carrier arranged radially with respect to the wafer edge. The carrier is positionable with respect to the edge of the wafer such that the first camera is opposite to the upper surface of the wafer edge and the third camera is opposite to the lower surface of the wafer edge. The second camera is stationary with respect to the front surface of the wafer.

In another embodiment, all three cameras are arranged on a carrier movable in a perpendicular direction with respect to the wafer edge.

The illumination means forming a bright field arrangement together with the cameras may be designed, for example, as a calotte having a diffusely transparent screen or a diffuser. The calotte is essentially cylindrical and has at least one recess so that the calotte partially surrounds the edge of the wafer. Several light sources may be arranged on the calotte. Thus a diffuse and even and homogeneous illumination of the edge area of the wafer is achieved by the cooperation of the several light sources and the diffusely transparent screen or the calotte.

The light sources may be designed as white light LEDs. It is further possible to provide each camera with its own light source. When arranging the cameras and the light sources, care must be taken to meet the conditions for the bright field illumination (the cameras are arranged in the angle of reflection of the light from the light sources). It is also advantageous if the light sources for the cameras consist of LEDs.

It is further advantageous if the wafer is deposited on a prealigner, wherein the prealigner positions the wafer in the field of view of one of the cameras. It is further advantageous if the prealigner is designed to be movable in the Z-direction, so that the thickness and the position of the wafer in the Z-coordinate direction may be determined with the second camera.

The method is advantageous if a wafer is deposited on a prealigner by a robot. Furthermore, at least a first camera and a third camera are arranged to be movable in a perpendicular direction with respect to a front surface of the wafer, so that the edge area of the wafer gets into the field of view of the respective camera. The wafer is positioned based on stored and/or determined position data such that the defects on the edge of the wafer are aligned with the field of view of the first and/or the second and/or the third camera for visual evaluation. With at least one of the cameras, the image acquisition is performed depending on the position of the defect on the upper surface of the wafer edge or the lower surface of the wafer edge or the front surface of the wafer edge. The image acquisition is performed in the bright field. The images acquired by the cameras may be displayed to the user on a display for visual inspection.

In order to facilitate the deposition of the wafer on the prealigner by the robot, it is advantageous if at least the first camera and the third camera are designed to be movable in the direction towards the wafer edge. The movement of the cameras towards the wafer edge may achieve that the area for the deposition of the wafer by the robot is free of any obstacles and that damage to the wafer or misdeposition of the wafer on the prealigner is thus avoided to a maximum extent. The first camera and the third camera are mounted on a carrier that is positioned in a perpendicular direction with respect to the wafer edge by the movable carrier. In the embodiment suggested here, the second camera is arranged stationary with respect to the front surface of the wafer. It is also contemplated that all three cameras are arranged on a common and movable carrier.

The three cameras are arranged in one plane. Also, the LEDs on the cylindrical calotte are arranged in another plane. The two planes are arranged at an angle with each other so that the conditions for a bright field arrangement are met.

The light sources may be formed of several LEDs emitting light of different wavelengths so that light of any color may be mixed for illumination.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
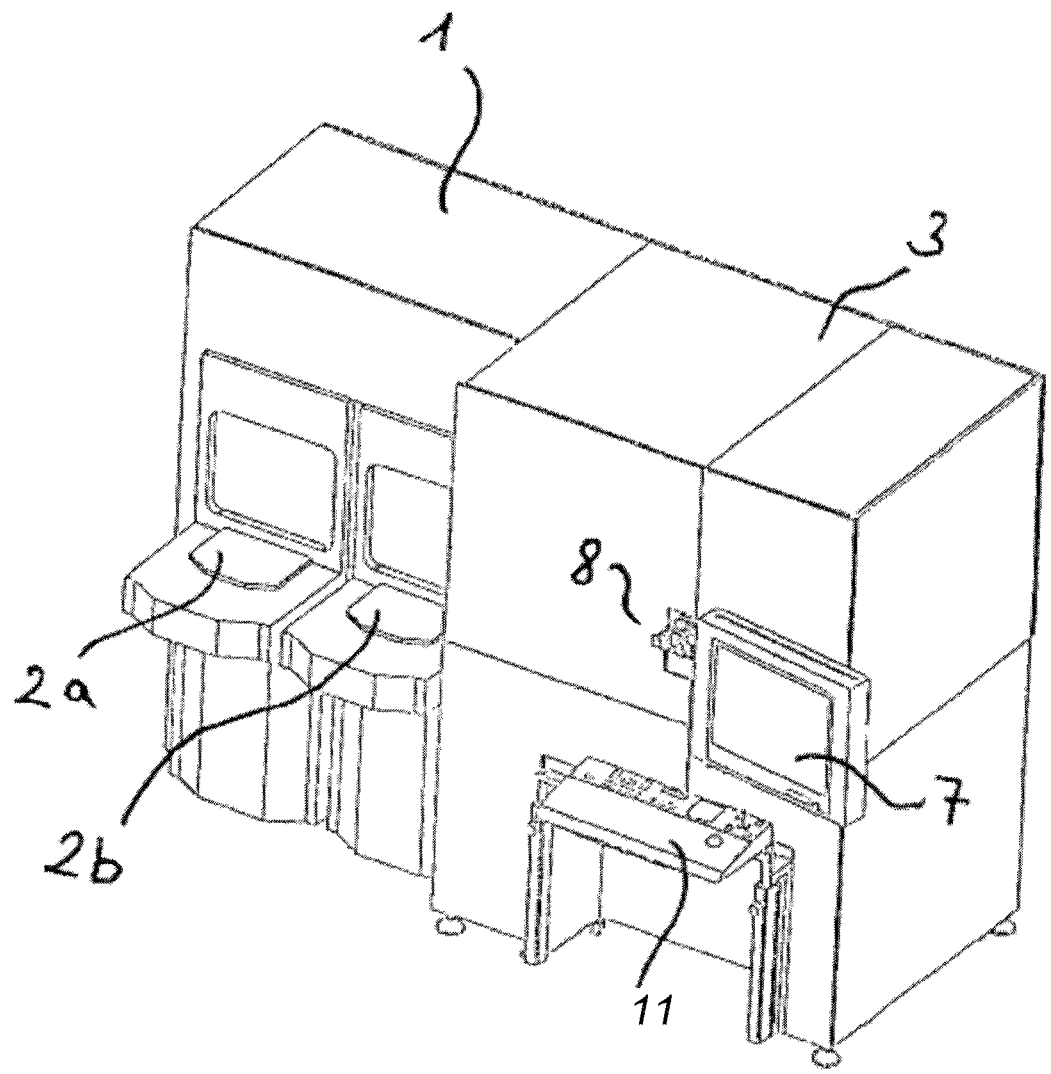
FIG. 1 shows a schematic representation of inspection system for wafers.

FIG. 1 exemplarily shows a 3D representation of a substrate supply module 1 and a work station 3. The general exterior view of the means also shows a monitor 7 (or display)

helping the user to check the data input via an operator input 11 or to monitor the status of the handling of wafer 6. Furthermore, the images acquired by the device for visually evaluating defects in the edge area of the wafer 6 may be displayed to the user on the display 7. The system for wafer inspection is further provided with a microscope (not shown), with which micro-inspection of defects on the surface of the wafer 6 is possible. Furthermore, a microscope view unit 8 may be available to the user, where detailed images of the substrate may be observed by the user. Wafers may be input into the wafer inspection machine via two load ports 2a, 2b (any other number of load ports is conceivable, and the illustration in FIG. 1 is not to be regarded as limiting).

Figure 2:
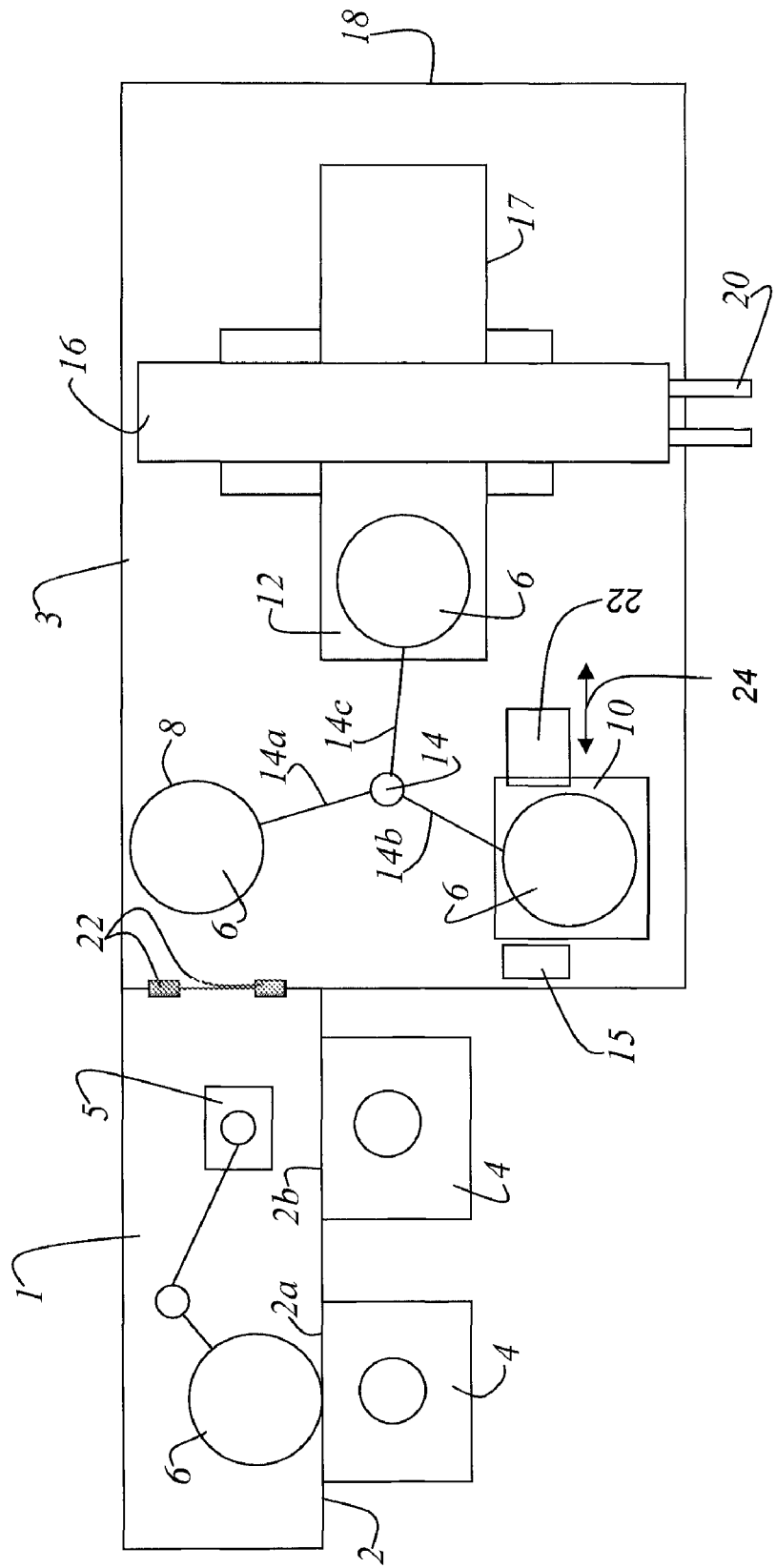
FIG. 2 shows a schematic view of the inner structure of inspection system for wafers.

FIG. 2 schematically shows the inner structure of system for inspecting wafers 6. A substrate supply module 1 is laterally associated with means 3. Means 3 for wafer inspection includes several work stations 9, 10 and 12. In this embodiment, the substrate supply module 1 is oriented with respect to means 3 such that it may be loaded with substrates from its front 2 via one or more load ports 2a, 2b. Open design or closed cartridges 4 are used, which are inserted into the load ports 2a, 2b manually by the user or by automation, e.g. by means of a robot. The cartridges 4 may be filled with wafers 6, or they may also be empty, depending on the intended work process. For example, all cartridges 4 may be filled, and wafers 6 are first taken from one cartridge, inserted into means 3 and returned to the same cartridge 4 after processing and inspection there.

Predetermined examinations, checks and inspections of the wafer are performed at the work stations 9, 10 and 12. In the present embodiment, three work stations 9, 10 and 12 are provided in means 3. In the center between the work stations 9, 10 and 12, a changer 14 is provided distributing the wafer 6 to the various work stations 9, 10 and 12. The changer 14 has three arms 14a, 14b and 14c. The first work station 9 serves for receiving the wafers 6 from the substrate supply module. The wafers 6 from the system for wafer inspection may also be returned to the substrate supply module at the first work station 9. The second work station 10 serves for aligning, for determining the positioning and/or for visually inspecting the wafers 6. For the alignment of the wafers 6, the second work station 10 is associated with measuring means detecting the markers applied to the wafer 6 and determining codings of the wafers. The measuring means 15 further determines the deviation from the exact positional deposition of the wafer 6 in the second work station 10. This work station will be referred to as prealigner 10 in the following description. The measuring means 15 determines the lateral run-out of the wafer 6 resulting from the imprecise deposition of the wafer 6 on the prealigner 10 by the three-paddle handler 14. The center offset of the wafer 6 is corrected by the prealigner 10. The data thus determined are forwarded to a central processing unit (not shown). The third work station 12 is designed for micro-inspection of the wafers 6. The third work station 12 has an X, Y table 17 supplying a microscope 16 for micro-inspection for the wafer 6. Z-adjustment may also be allowed by the X, Y table. The second work station 10 is also associated with the device 22 for visually inspecting wafers in the edge area of the wafer 6. As also shown in FIG. 2, the device 22 for visually inspecting wafers in the edge area of the wafer 6 may be moved towards the edge 8 of the wafer 6 or away from the edge 8 of the wafer in the direction of double arrow 24.

Figure 3:
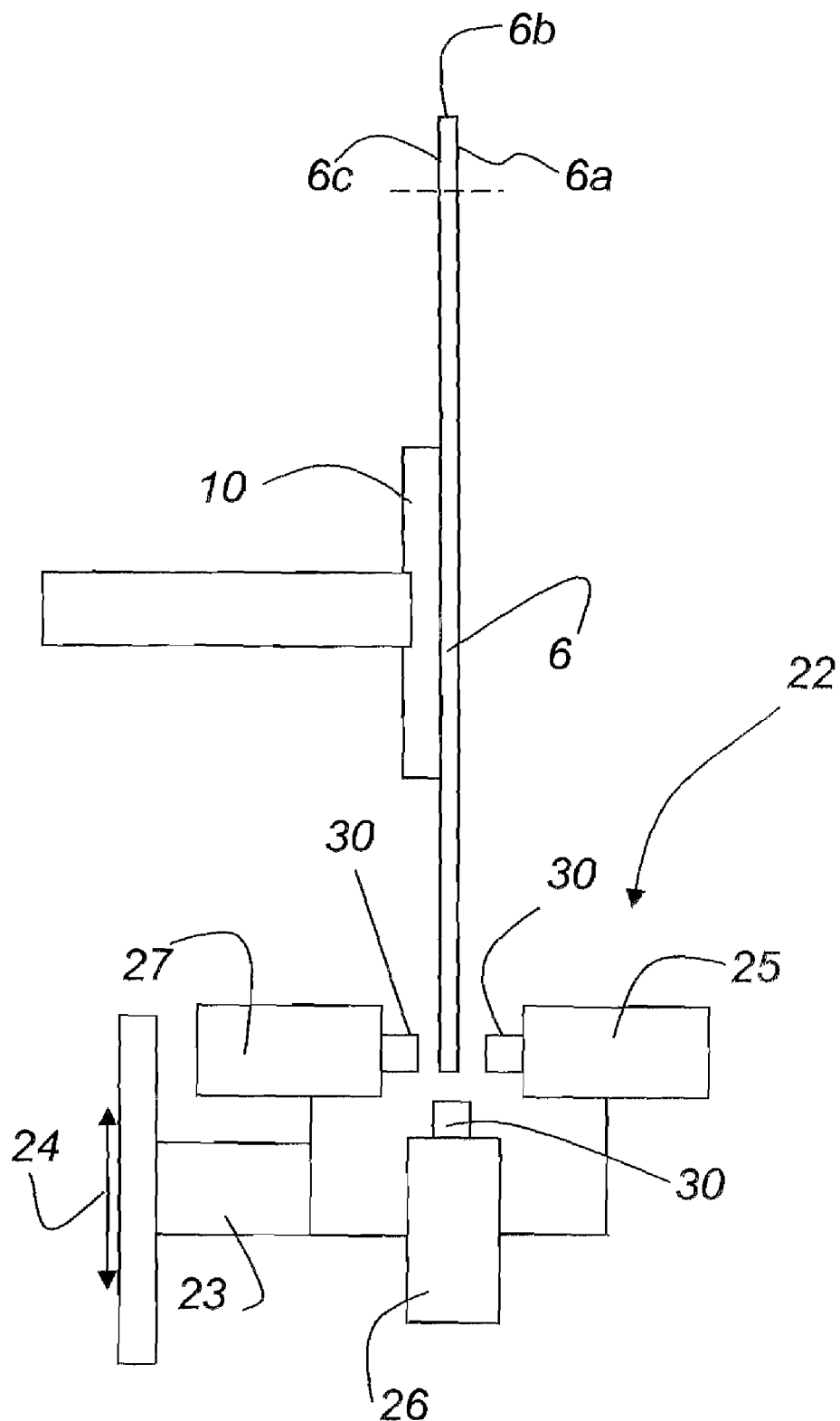
FIG. 3 shows a schematic representation of the arrangement of the device for visually inspecting defects in the edge area of a wafer.

FIG. 3 shows a schematic representation of the device for visually evaluating defects in the edge area of a wafer 6. The wafer 6 is deposited on the prealigner 10. As already mentioned in FIG. 2, the prealigner is disposed in system for inspecting wafers 6. A first camera 25, a second camera 26 and a third camera 27 are arranged on a common carrier 23. The common carrier 23 may be moved in a radial direction with respect to the wafer 6. Each camera 25, 26 and 27 is provided with an objective 30. The direction of movement is indicated by double arrow 24. The distance covered by the common carrier 23 ranges between 30 mm and 40 mm.

The cameras 25, 26 and 27 are designed as CCD cameras. The optical resolution depends on the size of the aperture used. The upper edge area 6a of the wafer 6 and the lower edge area 6c of the wafer 6 have a width 90 in the range of some millimeters. The front surface 6b of the wafer to be inspected has a wafer thickness of about 1 mm. The inventive device is used to capture the defects 88 located in the upper edge area 6a, the lower edge area 6c and on the front surface 6b of the wafer 6.

Figure 4:
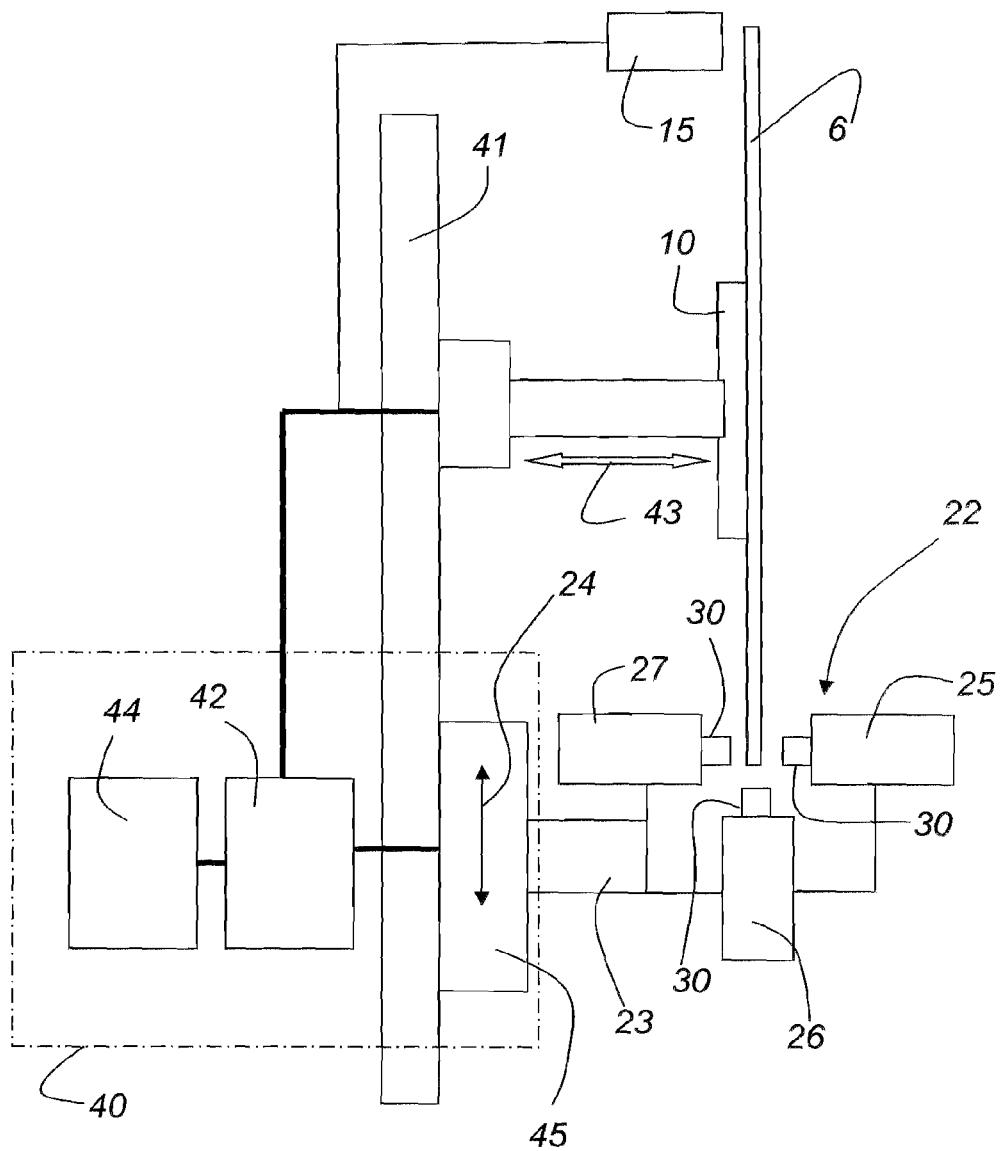
FIG. 4 shows an embodiment of the device for visually inspecting defects in the edge area of the wafer, wherein control elements are shown in addition to FIG. 3.

FIG. 4 shows a representation of the inventive device, which is provided with a controller 40 regulating the mechanical movement of the arrangement of the three cameras 25, 26 and 27. The controller 40 is also responsible for the controlled rotation of the prealigner 10. As already mentioned in the description for FIG. 2, the wafer 6 is deposited on the prealigner 10 by means of the three-paddle handler 14. As shown in FIG. 2, the prealigner 10 is also associated with at least one measuring device 15 determining the lateral run-out of the wafer 6. A center offset of the wafer 6 may be corrected by briefly lifting and correcting the wafer 6 by means of the three-paddle handler 14. In the embodiment shown, the three cameras 25, 26 and 27 of the device for visually observing defects in the edge area 6a, 6b or 6c of the wafer 6 are arranged on a common carrier 23. The common carrier 23 may be moved in a radial direction with respect to the wafer 6 in the direction of double arrow 24 by means of a translating unit 45. In the case that all three cameras 25, 26 and 27 are arranged on the common carrier 23, these three cameras are correspondingly moved towards the wafer 6 or away from the wafer 6. The prealigner 10 and the translating unit 45 are arranged on a common base plate 41. The prealigner 10 is also movable in an axial direction, as illustrated by double arrow 43. By the movement of the prealigner 10, the position of the wafer 6 with respect to the objectives 30 of the cameras 25, 26 and 27 may thus be set and/or changed. The drive assembly 40 is formed by the drive unit 45, the drive electronics 42 and the software driver 43. The raising and lowering movement of the prealigner 10 in the direction of double arrow 43 is also controlled by the drive electronics 42. With the help of image processing, the front surface of the wafer 6 is moved into the image center of the second camera 26 by raising the prealigner 10. At the same time, a predetermined position of the edge of the wafer 6 within a defined zone (6 mm width of the wafer edge) may be approached by rotating the prealigner 10. In this way, the defect to be examined is moved into the field of view of the first, second and/or third camera 25, 26, 27. The defect located at the position approached (on the upper surface of the edge of the wafer 6, the front surface of the edge of the wafer 6 and/or the lower surface of the edge of the wafer 6) may be captured by the first, second and/or third camera 25, 26 and 27. Each captured image may be presented for review on the display 7. Storage for later review is also contemplated. When all positions of a wafer where there are defects have been visited, the common carrier 23 is moved into the home position in the direction of double arrow 24 by means of a translating unit 45. The wafer may be removed from the prealigner 10 by the three-paddle handler 14, so that the next wafer 6 may be supplied to review. It will also be possible to copy the acquired images into the network of the user.

Figure 5:
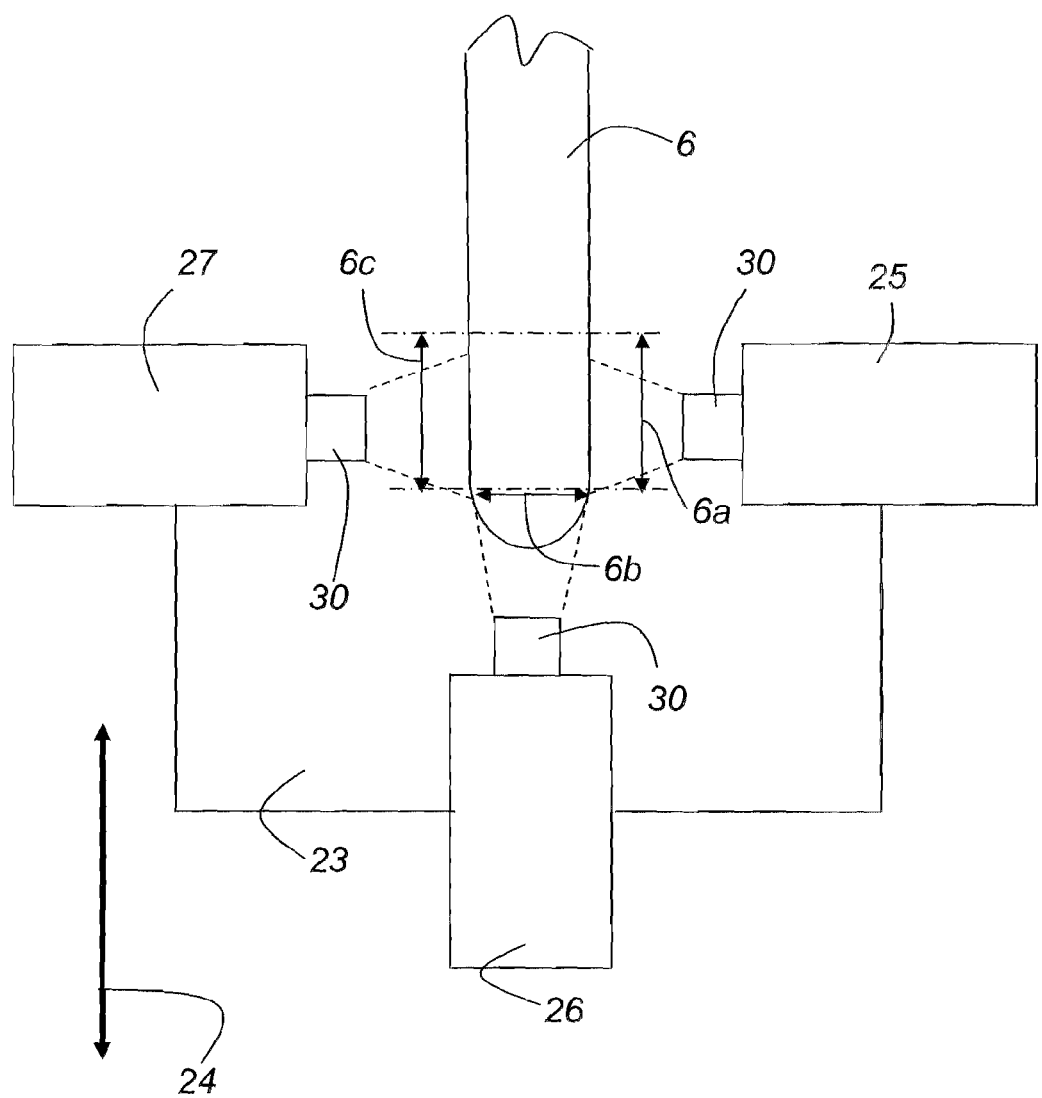
FIG. 5 shows an enlarged representation of the edge area of a wafer and the respective association of the three cameras with each area of the edge area of the wafer.

FIG. 5 shows an enlarged representation of the schematic arrangement of the three cameras 25, 26 and 27 with respect to the edge area of the wafer 6. In the embodiment shown, the three cameras 25, 26 and 27 are attached to a common carrier 23, which may be moved in a radial direction with respect to the edge of the wafer 6 in the direction of double arrow 24 shown in FIG. 5. By moving the common carrier 23, each of the cameras 25, 26 and 27 may be moved with respect to the wafer 6 so that it captures a particular area of the edge area of the wafer 6 with a field of view defined by the objective 30 (not shown). The first camera 25 is provided to capture an upper edge area 6a with the objective 30. The second camera 26 is designed with the objective 30 such that it captures the front surface 6b of the wafer 6. The third camera together with the objective 30 is designed such that it captures a lower edge area 6c of the lower surface of the wafer 6. As mentioned above, the viewing area of the first camera 25 and the third camera 27 for the upper edge area 6a and the lower edge area 6c is about 6 mm. The viewing area of the second camera 26 of the front surface 6b of the wafer 6 is about 1 mm, essentially corresponding to the thickness of the wafer 6.

Figure 6:
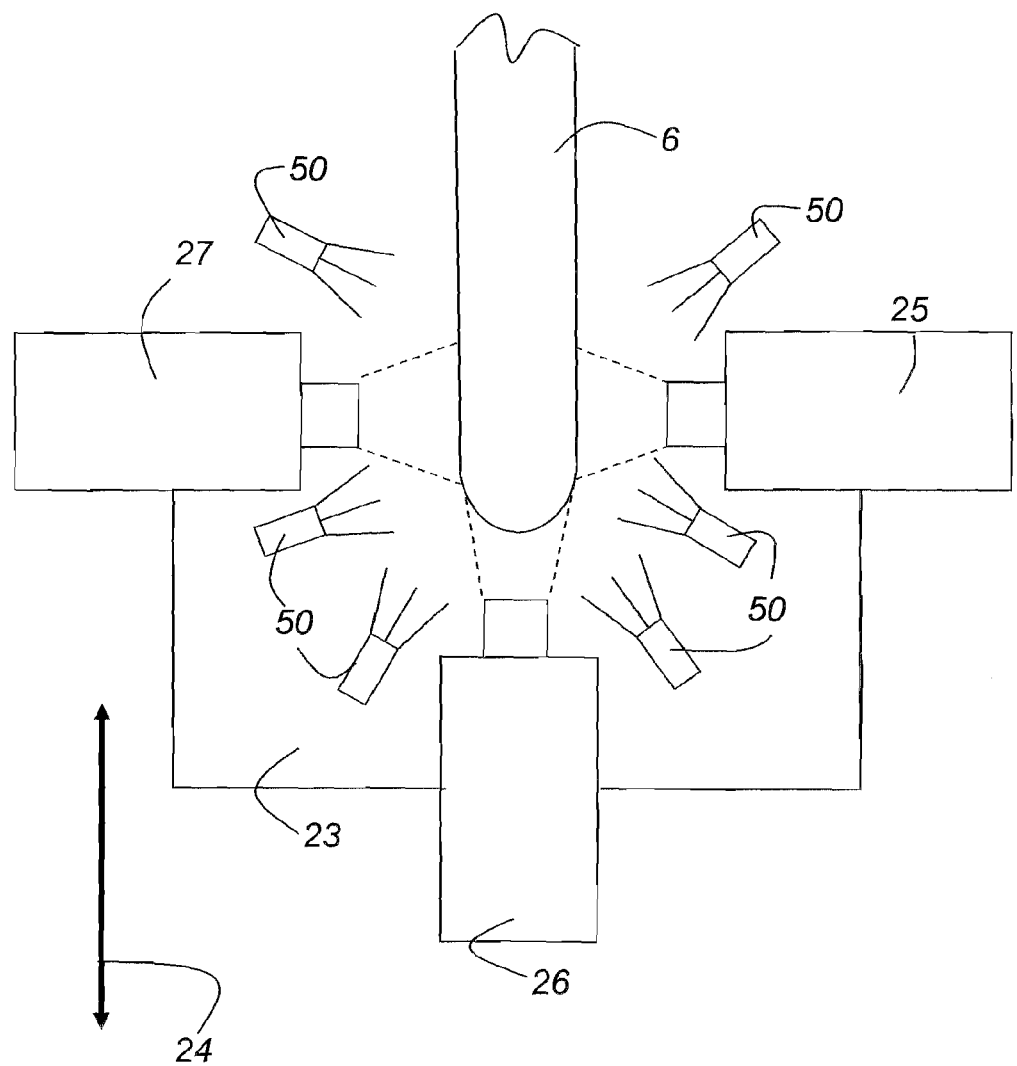
FIG. 6 shows a schematic representation of the edge area of the wafer and the association of the cameras with the edge area of the wafer, and also the arrangement of external illumination means constituting a bright field arrangement together with the cameras.

FIG. 6 shows a further embodiment of the arrangement of the three cameras 25, 26 and 27 with respect to the edge area of the wafer 6. In addition to the cameras 25, 26 and 27, there are provided several illumination means 50 illuminating the edge area 6a, 6b and 6c of the wafer 6. The illumination means 50 are arranged such that a bright field condition is met by their illumination and the arrangement of the cameras 25, 26 and 27.

Figure 7:
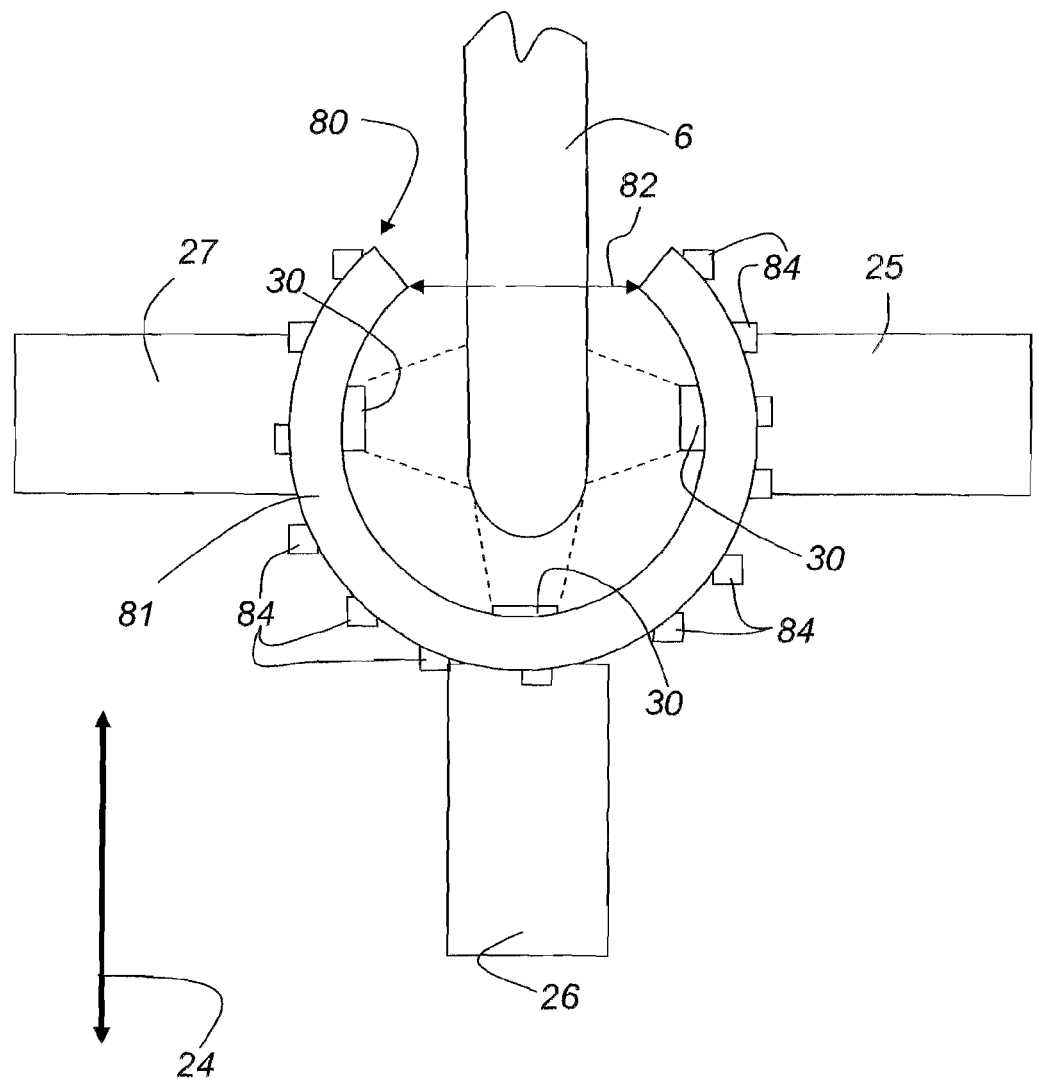
FIG. 7 shows a further embodiment of the illumination of the edge area of the wafer with a diffusely transparent screen.

FIG. 7 shows a further embodiment of the arrangement of the cameras 25, 26 and 27 and illumination means 80. The illumination means 80 is a calotte 81 to which a plurality of light sources are attached. The calotte 81 is provided with a diffusely transparent screen or diffuser (not shown) thus contributing to a more homogeneous illumination. The calotte 81 has a shape corresponding to the cross-section of a cylinder. The cameras 25, 26 and 27 and the calotte 81 are arranged on separate carriers, which are moved to the edge area of the wafer edge for capturing a defect. In the imaging position, the cameras 25, 26 and 27 and the required illumination are thus opposite to the lower surface, the front surface or the upper surface of the wafer 6. The calotte 81 comprises a recess 82 for imaging the edge of the wafer 6 in the interior of the calotte 81. The calotte 81 is provided with several illumination elements 84 or light sources. The illumination elements 84 are designed as LEDs emitting white light. A specific different wavelength and/or wavelength composition may be used for illuminating the edge of the wafer 6. The illumination elements 84 are arranged on the calotte 81 such that a bright field illumination of the edge of the wafer 6 is achieved.

In one embodiment, the cameras 25, 26 and 27 are attached to the calotte 81 such that the objectives 30 of the cameras 25, 26 and 27 are mounted in the calotte 81. In this embodiment, the calotte 81 functions as a carrier for the cameras and the several illumination elements 84. However, with this arrangement care must be taken that the bright field conditions are met to capture an area on the edge of the wafer 6.

Figure 8A:
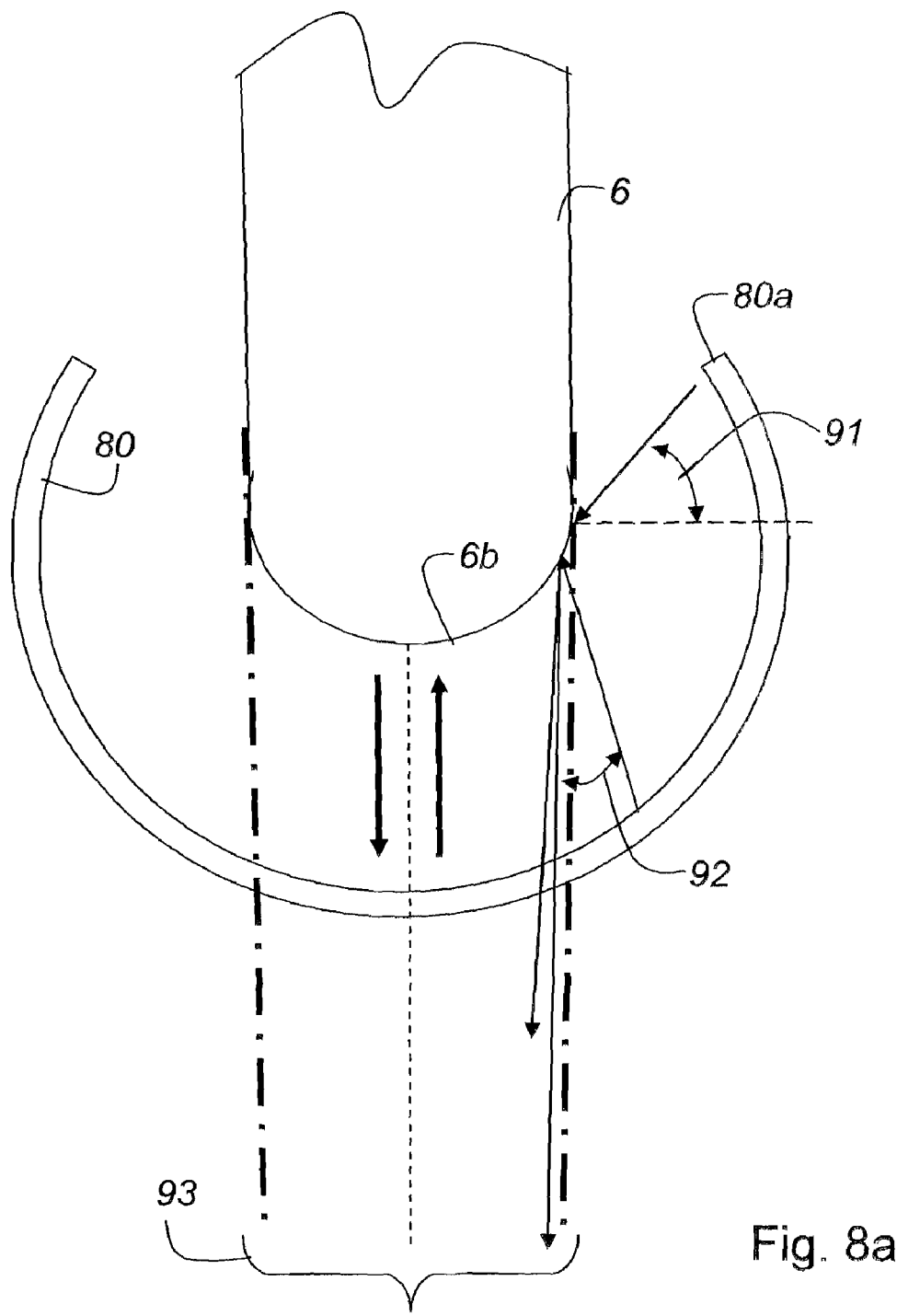
FIG. 8a shows a schematic representation of the illumination of the wafer in side view.

FIG. 8a shows a schematic representation of the illumination of the wafer 6 in side view. The screen (calotte) 81 provided with the LEDs as illumination elements surrounds part of the edge of the wafer 6. The illumination of the edge of the wafer 6 has to meet predetermined requirements to provide adequate conditions for the bright field arrangement with the cameras. The illumination angle 91 from the edge 80a of the screen 81 should be kept as large as possible. Likewise, the objective 30 of the cameras 25, 26 and 27 should be constructed as slender as possible, so that at least most of a light tube 93 defined by the illumination, which originates, for example, from the front surface 6b of the wafer 6, enters the objective 30, so that the conditions for bright field illumination are met.

Figure 8B:
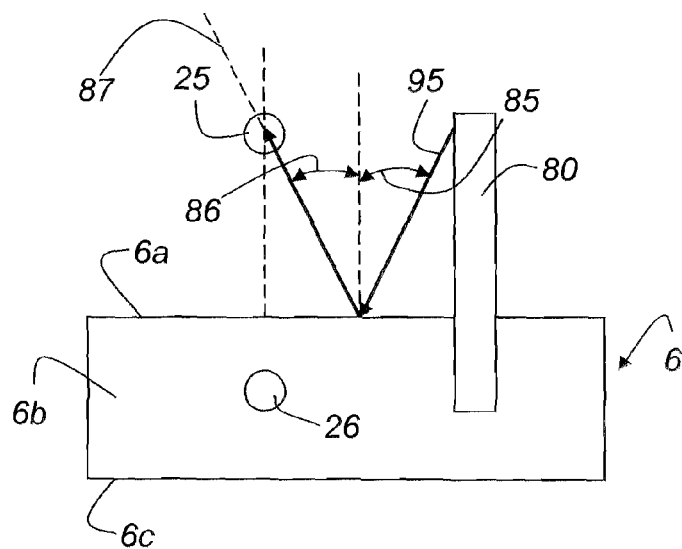
FIG. 8b shows a schematic representation of the illumination of the upper or lower surface of the edge of the wafer, the view onto the front surface of the wafer being shown.

FIG. 8b shows a schematic representation of the illumination of the upper or the lower edge area 6a or 6c of the wafer 6, the view onto the front surface 6b of the wafer being shown. From the calotte 81 or the illumination means 80, part of the light reaches the upper edge area 6a of the wafer 6. In this illustration, the first camera 25 and the second camera 26 are shown schematically as filled circles. The incident light 95 at the upper edge area 6a of the wafer 6 is designed such that the first camera 25 is in the bright field arrangement. The bright field arrangement is defined by the angle of incidence 85 of the light used for illumination being equal to the angle of reflection 86. The angle of reflection 86 is identical to the detection angle at which the optical axes 87 of the cameras 25, 26 or 27 are arranged for capturing the defects.

Figure 8C:
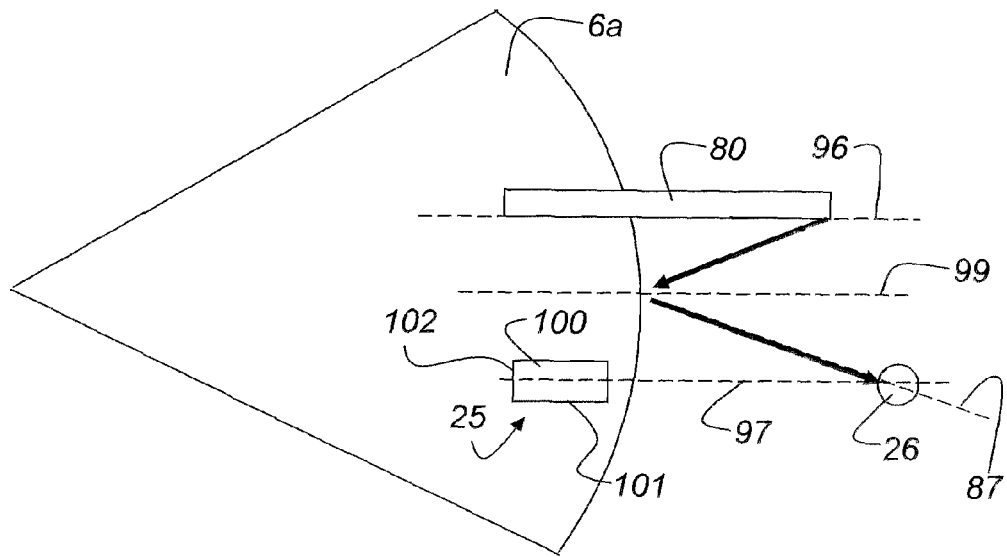
FIG. 8c shows a schematic top view of the illumination of the upper or lower surface of the edge of the wafer, the view onto the upper or lower surface of the wafer being shown.

FIG. 8c shows a schematic top view of the illumination of the upper or lower surface of the edge of the wafer 6. In FIG. 8c the view onto the upper edge area 6a of the wafer 6 is displayed. In this illustration, the position of the first camera 25 is illustrated by the rectangular shape of the CCD chip 100 of the first camera 25. In this illustration, the second camera 26 is illustrated schematically as a filled circle. The position of the LEDs in the screen 81 is represented by plane 96. The cameras 25, 26 and 27 are also arranged in a plane 97, which is at a symmetrical angle to the plane 96 of the LEDs (illumination elements 84). The plane 96 of the LEDs and the plane 97 of the cameras 25, 26 and 27 are both offset the same distance from the center line 99, so that the bright field conditions are met for the cameras 25, 26 and 27. The CCD chips 100 of the cameras 25, 26 and 27 have a long side length 101 and a short side length 102. The long side length 101 is parallel to the center line 99 in this embodiment.

Figure 9:
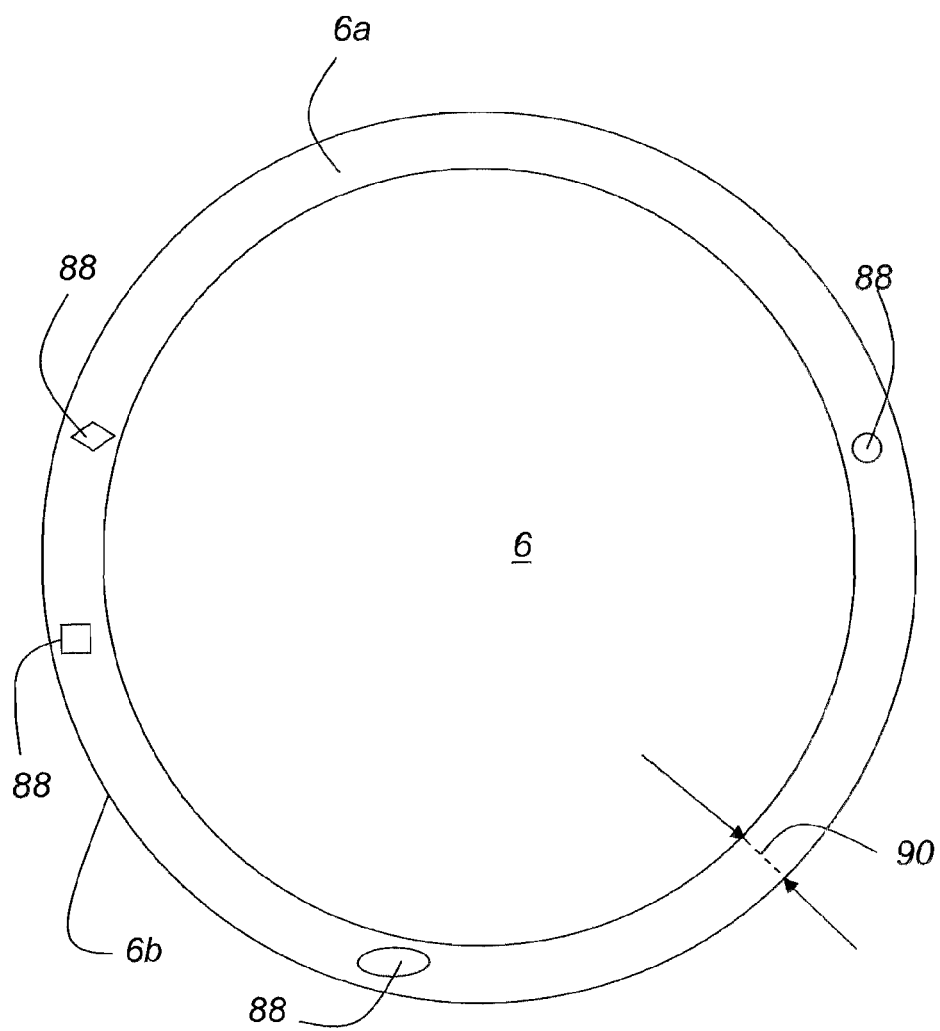
FIG. 9 shows a schematic view of a wafer, wherein several defects are symbolically depicted on the edge of the wafer.

FIG. 9 shows a top view of the upper surface of a wafer 6. The wafer 6 has an edge area 90 where several defects 88 may be located. The wafer 6 also has a front surface 6b which, as mentioned above, is opposite to the second camera 26 for capturing defects on the front surface 6b of the wafer 6.

As mentioned several times when describing the various embodiments of the arrangement of the cameras 25, 26 and 27, this arrangement allows viewing the front surface 6b of the wafer 6 and viewing the upper edge area 6a and the lower edge area 6c of the wafer 6. The wafer may be visually examined by the cameras 25, 26 and 27 in any rotational positions within the defined edge area 6a and 6c of several millimeters on the upper surface and on the lower surface.

The wafer 6 is deposited on the prealigner 10 by a three-paddle handler 14 existing in the inspection system. The lateral run-out of the wafer 6 is determined by means of a measuring device of the prealigner 10. The center offset may be corrected by briefly lifting and correcting the wafer 6 by means of the three-paddle handler 14. If this value is not achieved by the first correction handling, a second handling must be performed, i.e. the wafer 6 is again deposited on the prealigner 10. The device with the three cameras 25, 26 and 27 moves in a radial direction with respect to the wafer 6 over the edge of the wafer 6 and into the focus of the camera opposite to the front surface 6b of the wafer. With the help of image processing, the wafer 6 is moved into the image center of the field of view of the second camera 26 by raising the prealigner 10. This ensures that both the upper edge area 6a of the wafer 6 and the lower edge area 6c of the wafer 6 are in the focus of the camera 25 and 27, respectively. At the same time, the preselected position of the edge of the wafer 6 within the defined zone may be approached by rotating the prealigner 10. In other words, this means that, by rotating the prealigner 10, at least one defect gets into the field of view of one of the three cameras 25, 26 or 27. If, for example, a defect extends from the upper edge area 6a of the wafer 6 across the front surface 6b to the lower edge area 6c of the wafer 6, simultaneous imaging of this defect may be performed by all three cameras 25, 26, 27.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device for evaluating defects in the edge area of a wafer, with a first camera being arranged such that the first camera is opposite to an upper edge area of the wafer; a second camera being arranged such that the second camera is opposite to a front edge area of the wafer; a third camera being arranged such that the third camera is opposite to a lower edge area of the wafer; each camera has a field of view for acquiring an image of the respective area; at least one illumination means being arranges with respect to the first, the second and the third camera so that the first, the second and the third camera are in a bright field arrangement; and the wafer is positionable in the field of view of the respective camera for the acquisition of an image of the defect,
    wherein at least the first camera and the third camera are arranged on a carrier movable in a radial direction with respect to the wafer, wherein the carrier is positionable with respect to the edge of the wafer such that the first camera is opposite to the upper edge area of the wafer, and the third camera is opposite to the lower edge area of the wafer, and that the second camera is stationary with respect to the front edge area of the wafer.

2. The device according to claim 1, wherein the first, second and/or the third camera acquires an image of the defect in the edge area of the wafer with a defined field of view size, wherein the image acquisition is performed according to the position of the defect in the upper edge area of the wafer or in the lower edge area of the wafer or on the front edge area of the wafer.

3. The device according to claim 1, wherein all three cameras are arranged on a carrier moveable in a radial direction with respect to the wafer, wherein the carrier is positionable with respect to the edge of the wafer such that the first camera is opposite to the upper edge area of the wafer, the second camera is opposite to the front edge area of the wafer, and the third camera is opposite to the lower edge area of the wafer.

4. The device according to claim 1, wherein the illumination means includes a calotte to which the cameras are attached, and several illumination elements are arranged on the calotte for illuminating the wafer.

5. The device according to claim 4, wherein the illumination elements are white light LEDs associated with the calotte.

6. The device according to claim 4, wherein the illumination elements are formed of a plurality of LEDs emitting light of different wavelengths, so that light of any color is mixed.

7. The device according to claim 4, wherein the calotte has a cylindrical shape with a recess to surround the edge of the wafer.

8. The device according to claim 1, wherein the three cameras are arranged in one plane.

9. The device according to claim 8, wherein the plane where the cameras are located is inclined at an angle with respect to the plane where the LEDs are arranged, so that there is a bright field arrangement.

10. A method for evaluating defects in the edge area of a wafer with a first camera opposite to an upper edge area of the wafer, a second camera opposite to the front edge area of the wafer, and a third camera opposite to a lower edge area of the wafer, comprising the steps of:
    depositing a wafer on a prealigner by means of a robot,
    moving at least a first camera and a third camera in a radial direction with respect to the edge of the wafer so that the edge area of the wafer gets into a field of view of the respective camera,
    positioning the wafer based on stored and/or determined position data such that the defects on the edge of the wafer are aligned with the field of view of the first and/or the second and/or the third camera for visual evaluation, and
    beginning image acquisition with at least one of the cameras depending on the position of the defect opposite on the upper edge area of the wafer or the lower edge area of the wafer or the front edge area of the wafer, wherein each defect to be captured is illuminated in the bright field.

11. The method according to claim 10, wherein acquired images of the defects are displayed to the user on a display for visual inspection.

12. The method according to claim 10, wherein acquired images of the defects are stored in a database for later review of the images by the user.

13. The method according to claim 10, wherein acquired images of the defects are stored in a database, wherein an automatic evaluation of the defects is performed later on.

14. The method according to claim 10, wherein the three cameras are arranged on a carrier movable in a radial direction with respect to the edge of the wafer, wherein the carrier is positioned with respect to the edge of the wafer such that the first camera is opposite to the upper edge area of the wafer, the second camera is opposite to the front edge area of the wafer, and the third camera is opposite to the lower edge area of the wafer.

15. The method according to claim 10, wherein a prealigner is moved in a Z-coordinate direction to align the front edge area of the wafer with the field of view of the second camera so that the thickness of the wafer is measured.

16. The method according to claim 15, wherein the prealigner is moved in the Z-coordinate direction so that the upper edge area of the wafer and/or the lower edge area of the wafer is moved into the depth of focus area of the respective camera.

17. Use of a device for visually evaluating defects in the edge area of a wafer in inspection system for wafers; wherein the inspection system has at least one unit for micro-inspection; a transport means and an alignment means; at least one display on which acquired and/or stored images of the defects are displayed to a user; wherein the alignment means is associated with the device for visually evaluating defects in the edge area of the wafer, which has three cameras, wherein a first camera is arranged such that the first camera is opposite to an upper edge area of the wafer, wherein a second camera is arranged such that the second camera is opposite to a front edge area of the wafer, and wherein a third camera is arranged such that the third camera is opposite to a lower edge area of the wafer,
    wherein at least the first camera and the third camera are arranged on a carrier movable in a radial direction with respect to the wafer, wherein the carrier is positionable with respect to the edge of the wafer such that the first camera is opposite to the upper edge area of the wafer, and the third camera is opposite to the lower edge area of the wafer, and that the second camera is stationary with respect to the front edge area of the wafer.

18. The use according to claim 17, wherein at least one illumination means is arranged such that the at least one illumination means and the first, second and third camera are positioned in a bright field arrangement, and that the first, second and/or third camera acquires an image of a defect in the edge area of the wafer with a defined field of view size, wherein the image acquisition is performed depending on the position of the defect in the upper edge area of the wafer or in the lower edge area of the wafer or on the front edge area of the wafer, and the wafer is positioned in the field of view of the respective camera for acquiring the image of the defect.

19. The use according to claim 17, wherein the inspection system has several work stations and at least one substrate supply module.

20. The use according to claim 19, wherein the several work stations are constructed such that each performs a different inspection task on the wafer, and are grouped around a central unit, wherein the modules are designed such that they are interchangeable.

* * * * *